United States Patent

Giera et al.

Patent Number: 6,166,256
Date of Patent: Dec. 26, 2000

[54] PROCESS FOR PREPARING (4-NITROSOPHENYL)PHENYLHYDROXYLAMINE

[75] Inventors: Henry Giera, Grosskitzighofen; Carl Casser, Berlin; Pieter Ooms, Krefeld; Michael Schelhaas, Köln; Christian Laue, Monheim; Michaela Meiers; Gerhard Braun, both of Köln, all of Germany

[73] Assignee: Bayer Aktiengesellschaft, Leverkusen, Germany

[21] Appl. No.: 09/566,073

[22] Filed: May 8, 2000

[30] Foreign Application Priority Data

May 14, 1999 [DE] Germany ............... 199 22 405

[51] Int. Cl.[7] .................................. C07C 239/00
[52] U.S. Cl. ........................................ 564/300
[58] Field of Search ............................ 564/300

[56] References Cited

U.S. PATENT DOCUMENTS

4,129,740 12/1978 Zengel et al. ............... 560/48
4,242,523 12/1980 Battey et al. ............... 560/48

FOREIGN PATENT DOCUMENTS

1147237 4/1963 Germany.
1257984 12/1971 United Kingdom.

OTHER PUBLICATIONS

Chem. Ber. 31, Bamberger et al, (month unavailable) 1898, pp. 1513–1523, Das Verhalten Der Nitrosoalphyle gegen conc. Schwefelsäure.

J. Org. Chem. vol. 24, J. Boyer, (month unavailable) 1959, p. 2038, Oxidation of Nitroso–Aromatic Compounds with Peroxytrifluoroacetic Acid.

Z. Chem., 15, (month unavailable) 1975, Z. Wiechert, pp. 21–22, Das Verhalten aromatischer Nitrosoverbindungen in wasserfreiem flüssigem Fluorwasserstoff.

Liebigs Ann. Chem., (month unavailable) 1981, pp. 1271–1284, Aurich et al, Einfluss der Solvatisierung bei Umsetzungen von Nitrosobenzol mit Kalium–tert–butylat und anderen Basen.

J. Chem. Soc. (B) (month unavailable) 1968, J. Hutton et al, pp. 191–195, The Mechanism of Reduction of Nitrosobenzene by Alcohols.

Petroleum Chemistry, vol. 37, No. 5, (month unavailable) 1997, L.B. Kochetova et al, pp. 414–421, Mechanism of the Hydrogenation of Nitrobenzene: The Quantum–Chemical Approach.

*Primary Examiner*—Samuel Barts
*Attorney, Agent, or Firm*—Joseph C. Gil; Noland J. Cheung

[57] ABSTRACT

The present invention provides a process for preparing (4-nitroso-phenyl)phenyl-hydroxylamine which is characterized in that nitrobenzene is reacted in the presence of hydroxide and/or oxide-containing bases, optionally in the presence of solvents, at temperatures of 20 to 180° C. and pressures of 0.1 to 10 bar.

The process according to the invention has the particular advantage that it uses inexpensive and cost-effective nitrobenzene as starting material instead of the nitrosobenzene conventionally used hitherto.

7 Claims, No Drawings

PROCESS FOR PREPARING (4-NITRO-SOPHENYL)PHENYLHYDROXYLAMINE

FIELD OF THE INVENTION

The invention provides a process for preparing (4-nitrosophenyl)-phenylhydroxylamine which, as an intermediate in the preparation of 4-aminodiphenylamine (4-ADPA), can be used as an important feedstock for the synthesis of antioxidants and stabilizers in the rubber and polymer industry (Kirk-Othmer, Encyclopedia of Chemical Technology, 4th edition, 1992, vol. 3, pages 424–456; Ullmann's Encyclopedia of Industrial Chemistry, 5th edition, vol. A3, 1985, pages 91–111).

BACKGROUND OF THE INVENTION

Syntheses for (4-nitrosophenyl)phenylhydroxylamine, which have been previously described, have started only from nitrosobenzene. Nitrosobenzene is dimerized in strongly acid medium to give (4-nitrosophenyl) phenylhydroxylamine when the following acids are used, such as sulfuric acid (Bamberger et al., Chem. Ber., 31 (1898), 1513; DE 2020043), peroxytrifluoroacetic acid (Boyer, J. Org. Chem. 24 (1959) 2038), hydrofluoric acid (Wiechert, Z. Chem. 15 (1955) 21; DE 1147237), sulfonic acids, perchloric acid, trifluoroacetic acid (DE 2703919) and Lewis acids such as, for example, $BF_3xOEt_2$(EP 9267).

(4-nitrosophenyl)phenylhydroxylamine is also formed as a secondary product when reacting nitrosobenzene with alcoholates as bases, (Aurich et al., Liebigs Ann. Chem. (1981), 1271–1281; Hutton, Waters, J. Chem. Soc. (B) (1968) 191).

A serious disadvantage of the processes described is that they use nitrosobenzene as a starting material and this cannot be prepared in an economically viable manner, in particular, from inexpensive nitrobenzene, on an industrial scale (Kochetova, Klyuyev, Petroleum Chemistry, vol. 37, (1997), 414–421).

It was, therefore, desirable to develop a process for preparing (4-nitrosophenyl)phenylhydroxylamine which uses a more cost-effective and less expensive starting material than nitrosobenzene.

SUMMARY OF THE INVENTION

The present invention provides a process for preparing (4-nitrpsophenyl)phenylhydroxylamine which is characterized in that nitrobenzene is reacted with hydroxide and/or oxide group-containing bases, optionally in the presence of a solvent, at temperatures of 20 to 180° C. and pressures of 0.1 to 10 bar.

DETAILED DESCRIPTION OF THE INVENTION

Hydroxide and/or oxide group-containing bases which are suitable for use in the process according to the present invention are inorganic bases such as alkali metal hydroxides, alkali metal oxides, alkaline earth metal hydroxides, alkaline earth metal oxides and the corresponding hydroxides and oxides of the elements 58 to 71 in the Periodic System of the Elements (according to IUPAC, new). The following may be mentioned by way of example: the oxides and hydroxides of sodium, potassium, lithium, cesium, magnesium, calcium, barium, lanthanum and/or cerium, preferably the oxides and hydroxides of lithium, sodium, potassium cesium, most preferably, cesium hydroxide.

Furthermore, organic bases such as, for example, quaternary alkylammonium hydroxides ($NR_4^+OH^-$ with R representing, independently of each other, alkyl, aryl or aralkyl groups with 1 to 7 carbon atoms) are also suitable. The following examples may be mentioned: tetramethylammonium hydroxide, tetraethylammonium hydroxide, tetrapropylammonium hydroxide, tetrabutylammonium hydroxide, methyltributylammonium hydroxide, methyltripropylammonium hydroxide, methyltriethylammonium hydroxide, trimethylbenzylammonium hydroxide. Tetrapropylammonium hydroxide and tetrabutylammonium hydroxide are preferred. Tetramethylammonium hydroxide is most preferred.

Obviously, it is also possible to use the bases as mixtures with each other. The most beneficial mixing ratio can easily be determined each time in appropriate preliminary trials. Furthermore, it is possible to use the inorganic bases in combination with phase transfer catalysts. Suitable phase transfer catalysts are described, for example, in W. E. Keller, Fluka-Kompendium, vol. 1,2,3, Georg Thieme Verlag, Stuttgart 1986, 1987, 1992. For example, the previously mentioned bases may be used together with a crown ether such as 18-crown-6 or quaternary ammonium compounds. The bases to be used according to the present invention may have a water content of up to 6 mol of water; in a preferred embodiment, up to 3 mol of water; and in a most preferred embodiment, up to 2.5 mol of water, with respect to one mol of base. A higher water content generally impairs the yields.

According to the present invention, bases may be added in the solid form, as molten materials or as a solution or mixture in a solvent or solvent mixture.

According to the present invention, the bases are used in amounts of 0.01 to 3, preferably 0.1 to 2 equivalents per mol of nitrobenzene.

Suitable solvents are aromatic hydrocarbons with 6 to 20 carbon atoms, linear or cyclic ethers with up to 5 oxygen atoms and 2 to 16 carbon atoms, aromatic halogenated hydrocarbons with 6 to 20 carbon atoms and amides with 1 to 10 carbon atoms. Obviously, the solvents mentioned may be used as mixtures with each other. The following may be mentioned, in particular, as suitable solvents: benzene, toluene, xylene, tert.-butyl methyl ether, tert.-amyl methyl ether, diisopropyl ether, diethylene glycol dimethyl ether, glycol dimethyl ether, dioxan, tetrahydrofuran, diamyl ether, chlorobenzene, dichlorobenzene, dimethylformamide, dimethylacetamide and N-methylpyrrolidinone. The following are preferably used: toluene, xylene, glycol dimethyl ether, tert.-butyl methyl ether, diisopropyl ether, diethylene glycol dimethyl ether, most preferably tert.-butyl methyl ether and toluene. The amount of solvent is not a critical factor in the process according to the present invention. The most appropriate amount can also easily be determined in appropriate preliminary tests. The amount of solvent depends, in particular, on the reaction temperature and on the type and amounts of bases and catalysts used. Generally, the solvent is used in amounts of 1 to 99 wt. %, preferably 5 to 95 wt. %, and most preferably 15 to 90 wt. %, with respect to the total amount of reaction mixture.

The reaction temperatures for the process according to the present invention are preferably 20 to 180° C., and most preferably from 50 to 150° C.

It is an advantage to control the concentration of protic material, such as e.g. water, which is achieved by using water-bonding reagents such as molecular sieves, KOH, $P_2O_5$, but also by stripping with an inert gas, by distilling off water under e.g. reduced pressure and preferably by azeotropic distillation.

It is also an advantage to minimize the concentration of oxygen in the reaction solution, which can be achieved by degassing the solutions and by a conventional protective gas technique using e.g. nitrogen and/or argon.

Isolation of the desired (4-nitrosophenyl) phenylhydroxylamine from the reaction mixture takes place by crystallization, optionally after previous filtration or neutralization. However, it is also possible to use the reaction mixture obtained for further reaction without any further working-up procedures.

The reaction mixture obtained is suitable, in particular, for preparing 4-ADPA in the presence of hydrogen and hydrogenation catalysts. 4-ADPA can be used in the usual manner for the preparation of anti-ageing compounds, useful preferably in the rubber industry.

The invention is further illustrated but is not intended to be limited by the following examples in which all parts and percentages are by weight unless otherwise specified.

EXAMPLES

Example 1

123 g of nitrobenzene in 300 g of di-n-butyl ether are initially introduced. 140 g of tetramethylammonium hydroxide dihydrate are added to this solution. The reaction mixture is heated at 75–80° C. for four hours under an inert gas atmosphere. Using GC (internal standard) and HPLC (external standard), a selectivity of 16% for (4-nitrosophenyl)phenyl-hydroxylamine is determined at a conversion of 78%. After adding 50 ml of water, the phases separate. The aqueous phase is adjusted to pH=1 by adding 25% strength sulfuric acid and is extracted several times with methylene chloride. After concentrating by evaporation under vacuum, a residue of 85 g remains with a (4-nitrosophenyl)phenylhydroxylamine content of 14% (HPLC; external standard). This corresponds to a selectivity of 16%.

Example 2

7.4 g of tetramethylammonium hydroxide dihydrate and 10 g of molecular sieve were initially introduced into 50 ml of di-n-butyl ether. This mixture was heated to 80° C. under an inert gas atmosphere, 6.2 g of nitrobenzene were added and the mixture was stirred for 5 hours at this temperature. After adding 50 ml of water, 17% of (4-nitrosophenyl)phenyl-hydroxylamine was determined in the polar phase at 98% conversion, using HPLC.

Example 3

7.4 g of tetramethylammonium hydroxide dihydrate were initially introduced into 50 ml of triethylamine. This mixture was heated to 80° C. under an inert gas atmosphere, 6.2 g of nitrobenzene were added and the mixture was stirred for 5 hours at this temperature. After adding 50 ml of water, 14% of (4-nitrosophenyl)phenylhydroxylamine was determined in the polar phase at 84% conversion, using HPLC.

Example 4

22.2 g of tetramethylammonium hydroxide dihydrate were initially introduced into 50 ml of tert.-amyl methyl ether. This mixture was heated to 80° C. under an inert gas atmosphere, 6.2 g of nitrobenzene were added and the mixture was stirred for 2 hours at this temperature. After adding 50 ml of water, 9% of (4-nitrosophenyl)-phenylhydroxylamine was determined in the polar phase at 100% conversion, using HPLC.

Example 5

7.4 g of tetramethylammonium hydroxide dihydrate and 10 g of molecular sieve were initially introduced into 50 ml of tetrahydrofuran. This mixture was heated to reflux point under an inert gas atmosphere, 6.2 g of nitrobenzene were added and the mixture was boiled under reflux for 5 hours. After adding 50 ml of water, 8% of (4-nitrosophenyl)phenylhydroxyl-amine was determined in the polar phase at 77% conversion, using HPLC.

Example 6

3.7 g of tetramethylammonium hydroxide dihydrate and 10 g of molecular sieve were initially introduced into 50 ml of di-n-butyl ether. This mixture was heated to 80° C. under an inert gas atmosphere, 6.2 g of nitrobenzene were added and the mixture was stirred for 3 hours at this temperature. After adding 50 ml of water, 5% of (4-nitrosophenyl)phenyl-hydroxylamine was determined in the polar phase at 75% conversion, using HPLC.

Example 7

7.4 g of tetramethylammonium hydroxide dihydrate and 10 g of molecular sieve were initially introduced into 50 ml of tert.-butyl methyl ether. This mixture was heated to reflux point under an inert gas atmosphere, 6.2 g of nitrobenzene were added and the mixture was boiled under reflux for 3 hours. After adding 50 ml of water, 7% of (4-nitroso-phenyl)phenylhydroxylamine was determined in the polar phase at 65% conversion, using HPLC.

Example 8

7.4 g of tetramethylammonium hydroxide dihydrate and 10 g of molecular sieve were initially introduced into 50 ml of toluene. This mixture was heated to 80° C. under an inert gas atmosphere, 6.2 g of nitrobenzene were added and the mixture was stirred for 5 hours at this temperature. After adding 50 ml of water, 8% of (4-nitrpsophenyl)phenylhydroxylamine was determined in the polar phase at 95% conversion, using HPLC.

Example 9

7.4 g of tetramethylammonium hydroxide dihydrate and 10 g of molecular sieve were initially introduced into 50 ml of di-n-butyl ether. This mixture was heated to 65° C. under an inert gas atmosphere, 6.2 g of nitrobenzene were added and the mixture was stirred for 2 hours at this temperature. After adding 50 ml of water, 12% of (4-nitrosophenyl)phenyl-hydroxylamine was determined in the polar phase at 88% conversion, using HPLC.

Example 10

7.2 g of tetramethylammonium hydroxide dihydrate were initially introduced into 50 ml of tert.-amyl methyl ether. This mixture was heated to 80° C. under an inert gas atmosphere, 6.2 g of nitrobenzene were added and the mixture was stirred for 3 hours at this temperature. After adding 50 ml of water, 12% of (4-nitrosophenyl)phenylhydroxylamine was determined in the polar phase at 76% conversion, using HPLC.

Example 11

7.5 g of tetramethylammonium hydroxide dihydrate were initially introduced into a mixture of 50 ml of di-n-butyl ether and 10 ml of triethylamine. This mixture was heated to 80° C. (bath temperature) under an inert gas atmosphere, 6.2 g of nitrobenzene were added and the mixture was stirred for 5 hours at this temperature. After adding 25 ml of water, 15% of (4-nitrosophenyl)phenylhydroxylamine was determined in the polar phase at 79% conversion, using HPLC.

Example 12

61.6 g of tetramethylammonium hydroxide dihydrate were initially introduced into 48 ml of tert.-amyl methyl ether. This mixture was heated to 80° C. under an inert gas atmosphere, 63.6 g of nitrobenzene were added and the mixture was stirred for 4.5 hours at this temperature. 6% of (4-nitrosophenyl)-phenylhydroxylamine was determined in the polar phase at 67% conversion, using HPLC.

Example 13

85 g of the residue from example 1 are dissolved in 200 g of isopropanol and hydrogenated at 50° C. under 30 bar of $H_2$ until no more hydrogen is taken up, after adding 5 g of Pd/C (5% strength). After filtering off the catalyst, 0.055 mol of 4-ADPA are detected in the filtrate (GC, internal standard). This corresponds to a selectivity of 92% with respect to (4-nitrosophenyl)phenylhydroxylamine.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing (4-nitrosophenyl)phenylhydroxylamine comprising the step of reacting nitrobenzene with hydroxide and/or oxide-containing bases, optionally in the presence of solvents, at a temperature of 20 to 180° C. and a pressure of 0.1 to 10 bar.

2. A process according to claim 1, wherein said reaction is performed at a temperature of 50 to 150° C.

3. A process according to claim 1, wherein said nitrobenzene is reacted with hydroxide and/or oxide group-containing bases selected from the group consisting of alkali metal hydroxides, alkali metal oxides, alkaline earth metal hydroxides, alkaline earth metal oxides, the hydroxides and oxides of elements 58 to 71 of the Periodic System of Elements (IUPAC) and quaternary alkylammonium hydroxides and alcoholates.

4. A process according to claim 1, wherein said hydroxide and/or oxide group-containing base is a phase transfer catalyst combined with a source of a base.

5. A process according to claim 4, wherein said base is used in an amount of 0.01 to 3 equivalents per mol of nitrobenzene.

6. A process according to claim 1, comprising the step of controlling the water content of the reaction mixture by removing water.

7. A process for preparing 4-aminodiphenylamine comprising the step of reacting nitrobenzene with hydroxide and/or oxide-containing bases, optionally in the presence of solvents, at a temperature of 20 to 180° C. and a pressure of 0.1 to 10 bar to form (4-nitrosophenyl) phenylhydroxylamine; dissolving said (4-nitrosophenyl) phenylhydroxylamine in a solvent to form a solution; adding Pd/C to said solution; and hydrogenating said solution.

* * * * *